(12) United States Patent
Noto et al.

(10) Patent No.: US 9,788,730 B2
(45) Date of Patent: Oct. 17, 2017

(54) OPTICAL PROCESS AND APPARATUS FOR NON-INVASIVE DETECTION OF MELANOMA

(71) Applicant: DermaSensor, Inc., Delray Beach, FL (US)

(72) Inventors: John Noto, Lowell, MA (US); Robert Kerr, Shirley, MA (US); Maurice Ferre, Ft. Lauderdale, FL (US)

(73) Assignee: DERMASENSOR, INC., Delray Beach, FL (US)

( * ) Notice: Subject to any disclaimer, the term of this patent is extended or adjusted under 35 U.S.C. 154(b) by 392 days.

(21) Appl. No.: 13/788,595

(22) Filed: Mar. 7, 2013

(65) Prior Publication Data
US 2013/0253335 A1    Sep. 26, 2013

Related U.S. Application Data

(60) Provisional application No. 61/608,474, filed on Mar. 8, 2012, provisional application No. 61/720,908, filed on Oct. 31, 2012.

(51) Int. Cl.
*A61B 5/00* (2006.01)

(52) U.S. Cl.
CPC ............ *A61B 5/0075* (2013.01); *A61B 5/444* (2013.01); *A61B 5/0022* (2013.01); *A61B 5/0077* (2013.01); *A61B 5/6843* (2013.01); *A61B 5/6898* (2013.01); *A61B 5/7465* (2013.01)

(58) Field of Classification Search
CPC ... A61B 5/0075; A61B 5/6843; A61B 5/6898; A61B 5/444; A61B 5/0022; A61B 5/0077; A61B 5/7465
See application file for complete search history.

(56) References Cited

U.S. PATENT DOCUMENTS

| | | | |
|---|---|---|---|
| 5,175,697 A * | 12/1992 | Kawagoe et al. | 356/320 |
| 5,522,868 A | 6/1996 | Buckley et al. | |
| 5,555,885 A | 9/1996 | Chance | |
| 5,822,072 A | 10/1998 | Dai et al. | |
| 6,014,204 A | 1/2000 | Prahl et al. | |

(Continued)

OTHER PUBLICATIONS

Prince et al., "Analysis of spectroscopic diffuse reflectance plots for different skin conditions", Spectroscopy 24 (2010) 467-481.*

(Continued)

*Primary Examiner* — Katherine Fernandez
*Assistant Examiner* — Don N Ho
(74) *Attorney, Agent, or Firm* — The Marbury Law Group, PLLC

(57) ABSTRACT

A non-invasive, optical method and device for the detection of melanoma in skin lesions. The detection of the presence of melanoma is accomplished optically by looking for specific changes (signatures) in the spectrum of optical light elastically scattered off melanoma molecules. Elastic scattering spectroscopy (ESS) converts subcellular morphological changes into scattering spectrum signatures. A melanoma discrimination analysis is performed by illuminating the lesion with a handheld device that also collects a portion of the scattered light, converts it into digital signals, analyzes the requisite spectral signatures, and provides a logical output showing the user the presence (or absence) of melanoma in the subject lesion.

29 Claims, 7 Drawing Sheets

(56) References Cited

U.S. PATENT DOCUMENTS

| | | | |
|---|---|---|---|
| 6,015,969 | A | 1/2000 | Nathel et al. |
| 6,381,018 | B1 | 4/2002 | Bigio et al. |
| 7,822,468 | B2 | 10/2010 | Stamnes et al. |
| 2002/0183624 | A1* | 12/2002 | Rowe et al. .................. 600/476 |
| 2004/0161804 | A1* | 8/2004 | McCash et al. ............... 435/7.2 |
| 2006/0209200 | A1* | 9/2006 | Xu ................................ 348/294 |
| 2007/0073156 | A1* | 3/2007 | Zilberman .......... A61B 5/0064 600/473 |
| 2010/0185064 | A1* | 7/2010 | Bandic et al. ................ 600/306 |
| 2011/0261355 | A1* | 10/2011 | Hannel et al. ................ 356/303 |

OTHER PUBLICATIONS

Canpolat et al, "Diagnosis and Demarcation of Skin Malignancy Using Elastic Light Single-Scattering Spectroscopy: A Pilot Study", Dermatol Surg 2012;38:215-223.*

A'Amar, et al., "Comparison between ultraviolet-visible and near-infrared elastic scattering spectroscopy of chemically induced melanomas in an animal model", Journal of Biomedical Optics vol. 9, No. 6, pp. 1320-1326, (Nov./Dec. 2004).

Marchesini, et al., "In vivo Spectrophotometric Evaluation of Neoplastic and Non-Neoplastic Skin Pigmented Lesions—I. Reflectance Measurements", Photochemistry and Photobiology, vol. 53, No. 1, pp. 77-84, (1991).

Marchesini, et al., "In vivo Spectrophotometric Evaluation of Neoplastic and Non-Neoplastic Skin Pigmented Lesions. II: Discriminant Analysis Between Nevus and Melanoma", Photochemistry and Photobiology, vol. 55, No. 4, pp. 515-522, (1992).

Perelman, et al., "Observation of Periodic Fine Structure in Reflectance from Biological Tissue: A New Technique for Measuring Nuclear Size Distribution", Physical Review Letters, vol. 80, No. 3, pp. 627-630, (Jan. 19, 1998).

Wallace, et al., "Spectrophotometric assessment of pigmented skin lesions: methods and feature selection for evaluation of diagnostic performance", Phys. Med. Biol. 45, pp. 735-751, (2000).

Wolbarsht, et al., "Melanin, a unique biological absorber", Appl. Opt., vol. 20, No. 13, pp. 2174-2186, (Jul. 1, 1981).

Zonios, et al., "Diffuse reflectance spectroscopy of human adenomatous colon polyps in vivo", Applied Optics, vol. 38, No. 31, pp. 6628-6637, (Nov. 1, 1999).

* cited by examiner

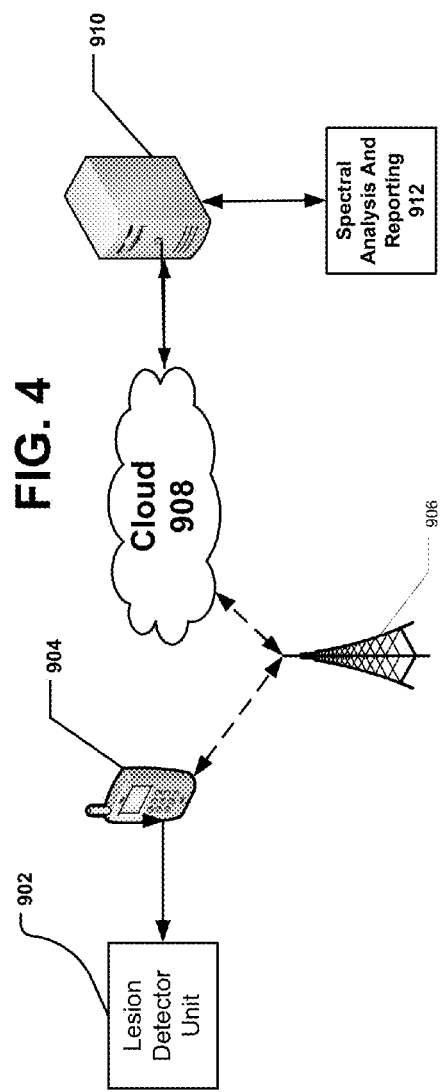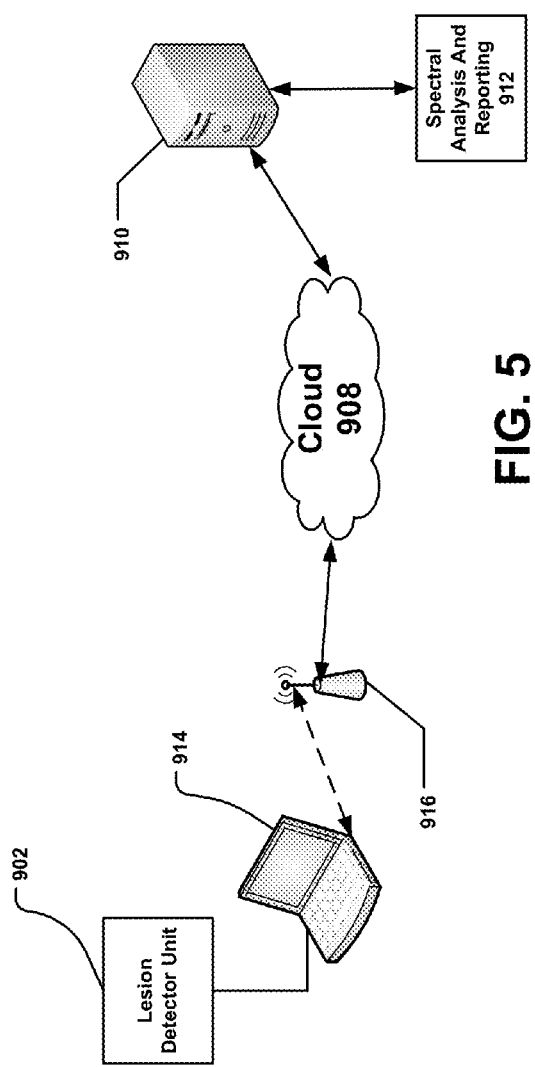

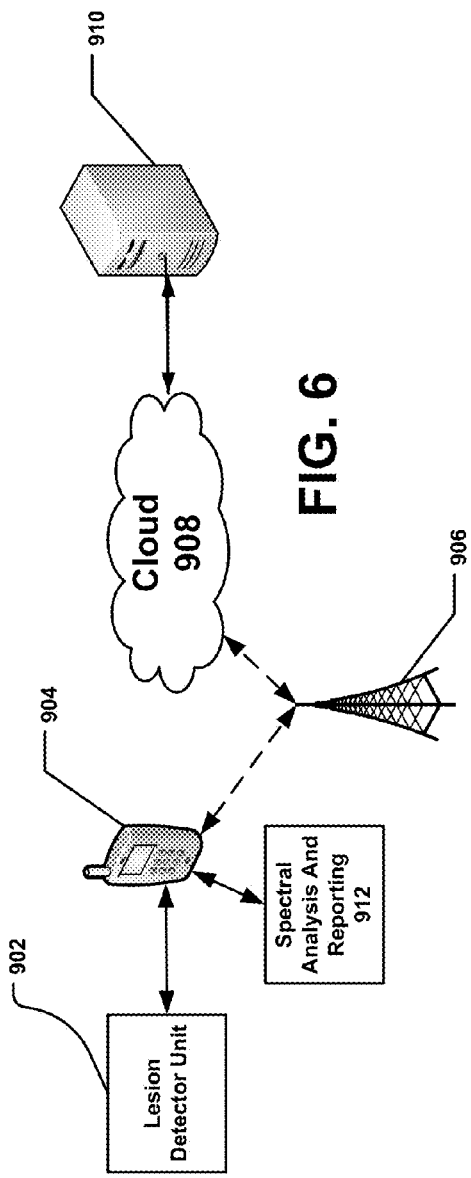
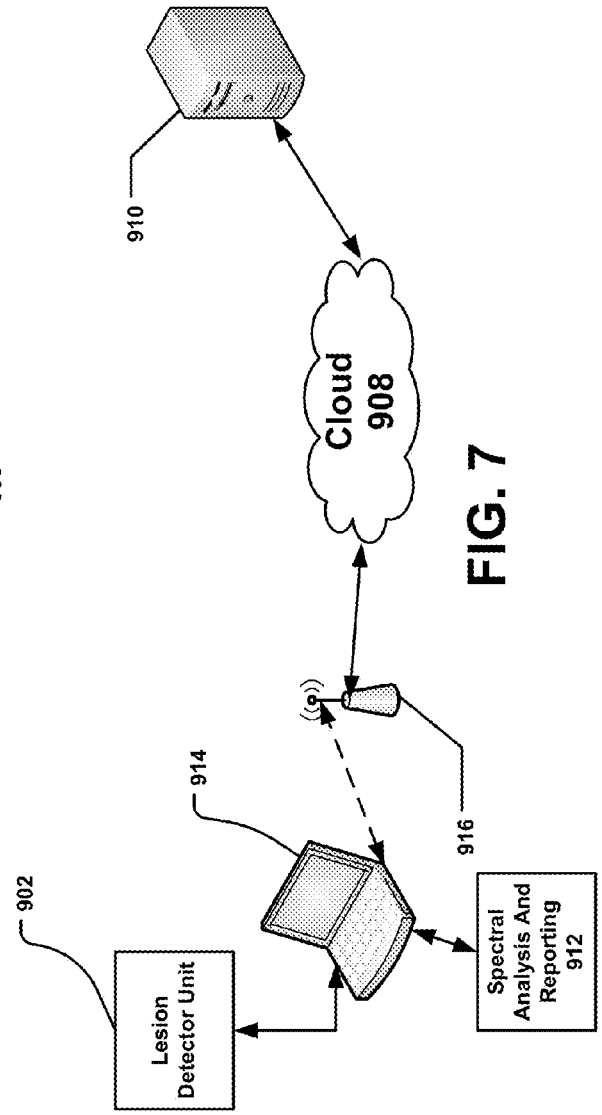

OPTICAL PROCESS AND APPARATUS FOR NON-INVASIVE DETECTION OF MELANOMA

CROSS REFERENCE TO RELATED APPLICATIONS

This application claims priority under 35 U.S.C. §119(e) from provisional application No. 61/608,474 filed Mar. 8, 2012, and from provisional application 61/720,908 filed Oct. 31, 2012, both of which are incorporated by reference herein, in their entireties, for all purposes.

BACKGROUND

The rising incidence of melanoma constitutes a significant public health risk. The close correlation between the trend of melanoma mortality and increasing radiation in the UV-B band at the Earth's surface is expected to continue until stratospheric ozone depletion, due to chlorofluorocarbon (CFC) deposition in prior decades, reaches a photochemical steady state in the middle of this century. Tumors detected while still in their early stages have a good prognosis.

However, the principal present clinical state of the art for diagnosing melanoma lesions is through biopsy and histopathology. This invasive, in-office procedure consists of freezing the lesion on the skin and extracting a portion of the subject lesion in a dermatology office. The extracted portion is then transferred to a histopathology laboratory for analysis. Such analysis typically involves examining visual features like size, symmetry, border irregularity and color (sometimes called the ABCD technique). The effort required for this technique makes it less than ideal as a first-line melanoma diagnostic.

SUMMARY

Melanoma and benign lesions modify the scattered light differently, changing the slopes and integrated intensities of the scattered spectrum in signature ways. Diffuse reflectance, or elastic scattering (ESS), can distinguish melanoma from benign skin lesions. Reflectance spectroscopy, or elastic scattering, shows high sensitivity and specificity in discriminating melanoma from benign lesions by analyzing the spectral characteristics of their scattered light spectrum over the near-UV to the near-IR wavelength range (approximately 300-950 nm). Further, the ability to discriminate wavelength (and therefore color) is also part of this technique illustrated in the various embodiments herein.

In an embodiment, a handheld device operating on these elastic scattering principles is illustrated as an in-home, office and/or remote early melanoma detection aid.

In an embodiment a broadband white light source may be directed to the lesion by means of a fiber optic cable, and collected upon scattering from the lesion by a second fiber optic cable. The collected scattered white light is sorted into wavelengths by a spectrometric element and read into an intensity spectrum (as a function of wavelength) by a detector. The detector output is analyzed by computer software to generate the intensity spectra used to determine the spectral signatures for melanoma.

In another embodiment, an illumination device is configured as a hand device that uses narrowband LED sources, miniature detectors, fiber optics, and processors comprising instructions that cause the processor to evaluate the incoming spectrum according to stored algorithms to provide a rapid assessment of the presence of melanoma cells.

DESCRIPTION OF THE DRAWINGS

FIG. 4 illustrates a smart phone with analysis being performed at a healthcare provider according to an embodiment.

FIG. 5 illustrates a laptop computer with analysis being performed at a healthcare provider according to an embodiment.

FIG. 6 illustrates a smart phone with analysis taking place on the smart phone with manual or automatic reporting to a healthcare provider according to an embodiment.

FIG. 7 illustrates a laptop with analysis taking place on the laptop with manual or automatic reporting to a healthcare provider according to an embodiment.

DETAILED DESCRIPTION

The various embodiments are described in detail with reference to the accompanying drawings. Wherever possible, the same reference numbers are used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

The term "mobile device" is used herein to refer to any or all of smartphones, personal data assistants (PDA's), laptop computers, tablet computers, ultrabooks, Internet enabled cellular telephones, and similar personal electronic devices which include a programmable processor and circuitry for receiving and processing information.

Figure 3:
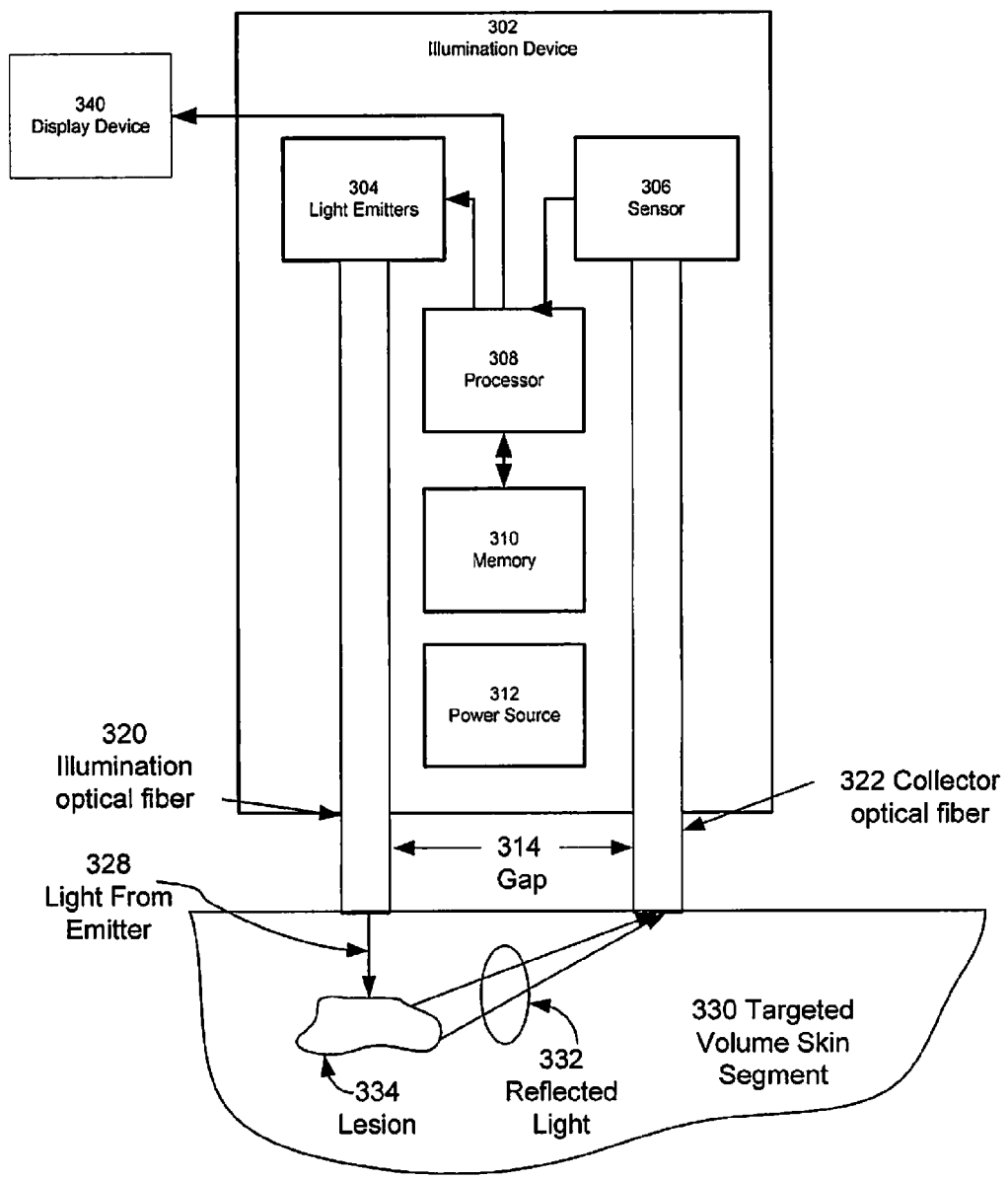
FIG. 3 is a block diagram illustrating an illumination device according an embodiment.

FIG. 3 is a block diagram illustrating an illumination device according an embodiment.

An illumination device 302 comprises a set of light emitters 304, a light sensor 306, a processor 308 and a memory 310 comprising instructions for the processor 308 and storage for data acquired by the sensor 306. It should be noted that in alternative embodiments illustrated herein, the processor forwards the reflectance information for subsequent processing and may not necessarily store the reflectance measurements.

The set of light emitters 304 provides illumination to a targeted volume skin segment 330 via an illumination optical fiber 320, such as for example, a 400-micron optical fiber. In an embodiment the illumination region is approximately 200-400 microns across. A large lesion may be evaluated by moving the illumination optical fiber 320 across the lesion. In an embodiment, the set of light emitters 304 are narrowband LED light sources. In another embodiment, the set of light emitters 304 are narrowband laser diodes. Other narrowband sources known in the art may also be useful in providing the illumination of the targeted area of skin.

In an embodiment, a broadband light source is used in conjunction with narrowband interference filters. The interference filter uses multiple layers to eliminate, by destructive interference, all light except within a prescribed band. The fabrication of the filter (number of layers, layer thickness, and so on) determines the width of the passband.

In an embodiment, each light emitter emits a specific wavelength between 300 nm and 950 nm (the very near UV to the very near IR range, including the visible), corresponding to wavelength bands important in distinguishing melanoma from benign elastic scattering. For example, a set of emitters within this range include discrete sources that emit light at 355 nm, 405 nm, 445 nm, 532 nm, 635 nm, 650 nm, and 808 nm. In another embodiment, an illumination device may be constructed using some or all of the emitters from the set of emitters, such as four or six emitters. The wavelengths may be selected based on the melanoma of interest (as determined by the spectral signatures) although this is not meant as a limitation.

The sensor 306 receives reflected light via a collection optical fiber 322, such as for example a 200-micron optical fiber. In an embodiment, the sensor 306 detects elastically scattered light and measures its intensity. The detected intensity is fed to a processor 308 that perform the calculations (described below), using the detected intensity, that allow the illumination device to distinguish between melanoma and benign lesion tissue.

The illumination optical fiber 320 and the collection optical fiber 322 are separated by a gap 314 that is optimized for maximum detection of scattered signal with minimum contamination from direct reflection and other factors. In an embodiment, this gap is approximately 800 microns.

In an embodiment, the illumination device 302 is configured as a handheld "light pen" (on the order of scale of a typical writing pen although this is not meant as a limitation) that illuminates the target lesion and detects the elastically scattered light.

In an embodiment, the memory 310 includes data that represent values of specific discriminators acquired from known cancerous lesions. For example, the discriminators may include (individually or in combination) individual wavelength spectral values, slopes between wavelengths, and areas under the curve.

Figure 1:
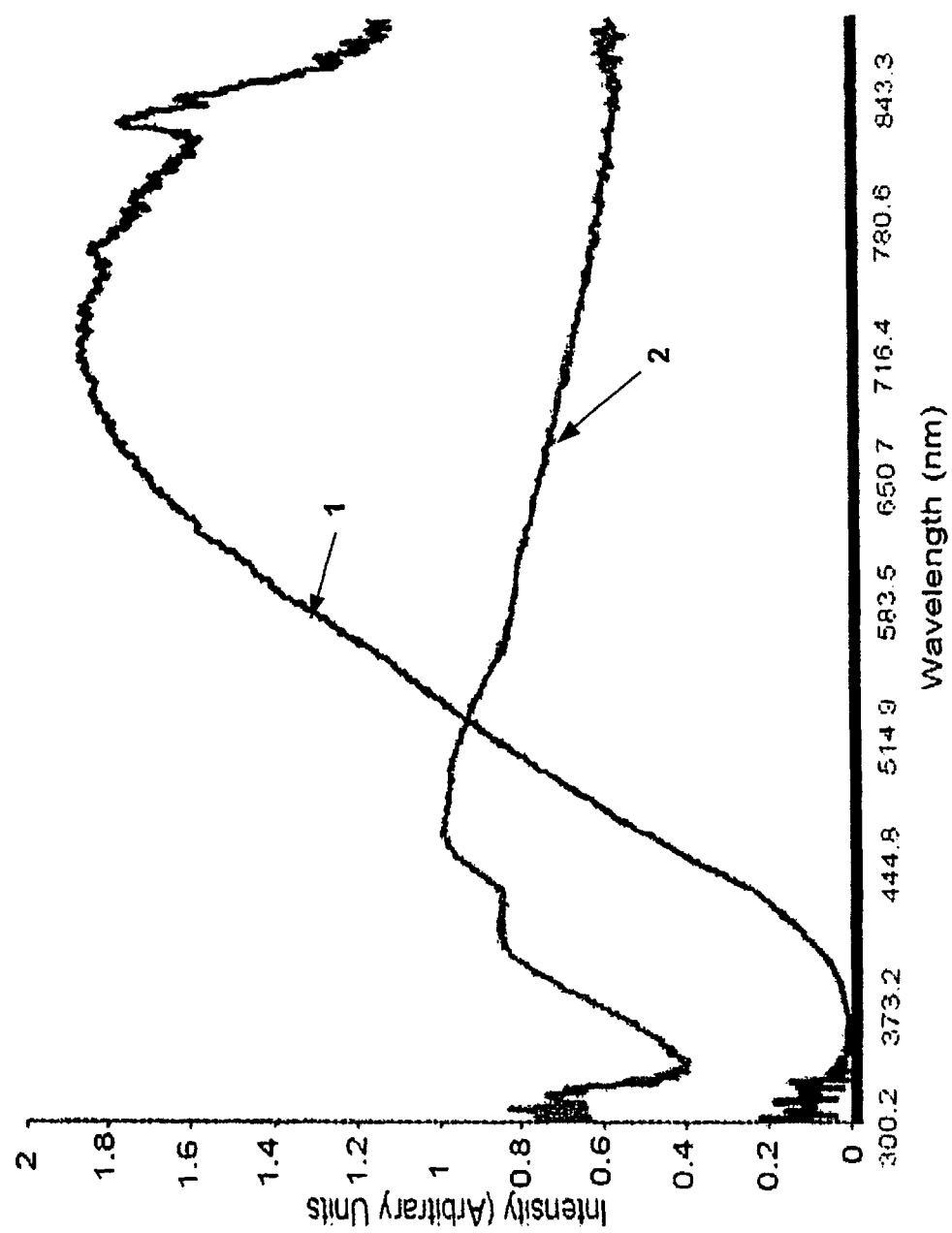
FIG. 1 is a comparison of the spectra for lesion and healthy skin, showing the differences in their scattering properties according to an embodiment.

Referring to FIG. 1, elastic scattering is compared between normal skin 2 and a subject lesion 1. Intensity function and spectrum slope are markedly different in the lesion scattering spectrum. Skin lesions contain higher concentrations of melanin, and the cellular and sub-cellular morphology of that melanin is altered in malignant melanoma compared to benign naevi. Hence, the spectral signatures of elastically scattered optical (very near-UV to very near-IR) light can provide information concerning the difference not only between normal skin and lesions, but between benign naevi and malignant melanoma. Melanocytic, or melanoma-containing, lesions tend to have different thickness (Breslow thickness) than benign lesions; and this difference in lesion thickness (as well as other microscopic architecture associated with melanoma) is likely to affect the ESS signal thus providing the ability to make an accurate diagnosis.

In an embodiment, spectral signatures identified in the elastically scattered light at a variety of wavelengths, individually or in combination, may be used for early detection of melanoma. By way of illustration and not by way of limitation, spectral signatures may be derived from:

Differences in reflectance/absorption at specific wavelengths. This signature is exemplified by structure that distinctly affects the scattered intensity at one or more different wavelengths.

Differences in the total integrated intensity over a range of wavelengths. This signature represents an area defined by between reflectance/absorption readings at different wavelengths of illumination. This effect is substantial over a range of tens (or even a hundred) nanometers.

Differences in average spectrum slope between multiple wavelengths. This difference is clearly demonstrated in FIG. 1 in the comparison between healthy skin and lesion skin. The healthy skin spectrum 2 (in addition to having some more distinct absorption features) is much more level on average than the spectrum 1 from the lesion tissue.

The reflectance spectrum of any skin can be expressed as a function of wavelength. The "effective reflectance spectrum" $R_E(\lambda)$ can be defined as:

$$R_E(\lambda) = \frac{R_L(\lambda)}{R_H(\lambda)} \quad (1)$$

where $R_L(\lambda)$ and $R_H(\lambda)$ are, respectively, the reflectance spectra for lesion skin and healthy skin. In an embodiment, a set of signatures may be four quantities of $R_E(\lambda)$ (with $\lambda$ in nm) that were determined via multivariate external discriminant analysis.

Figure 2:
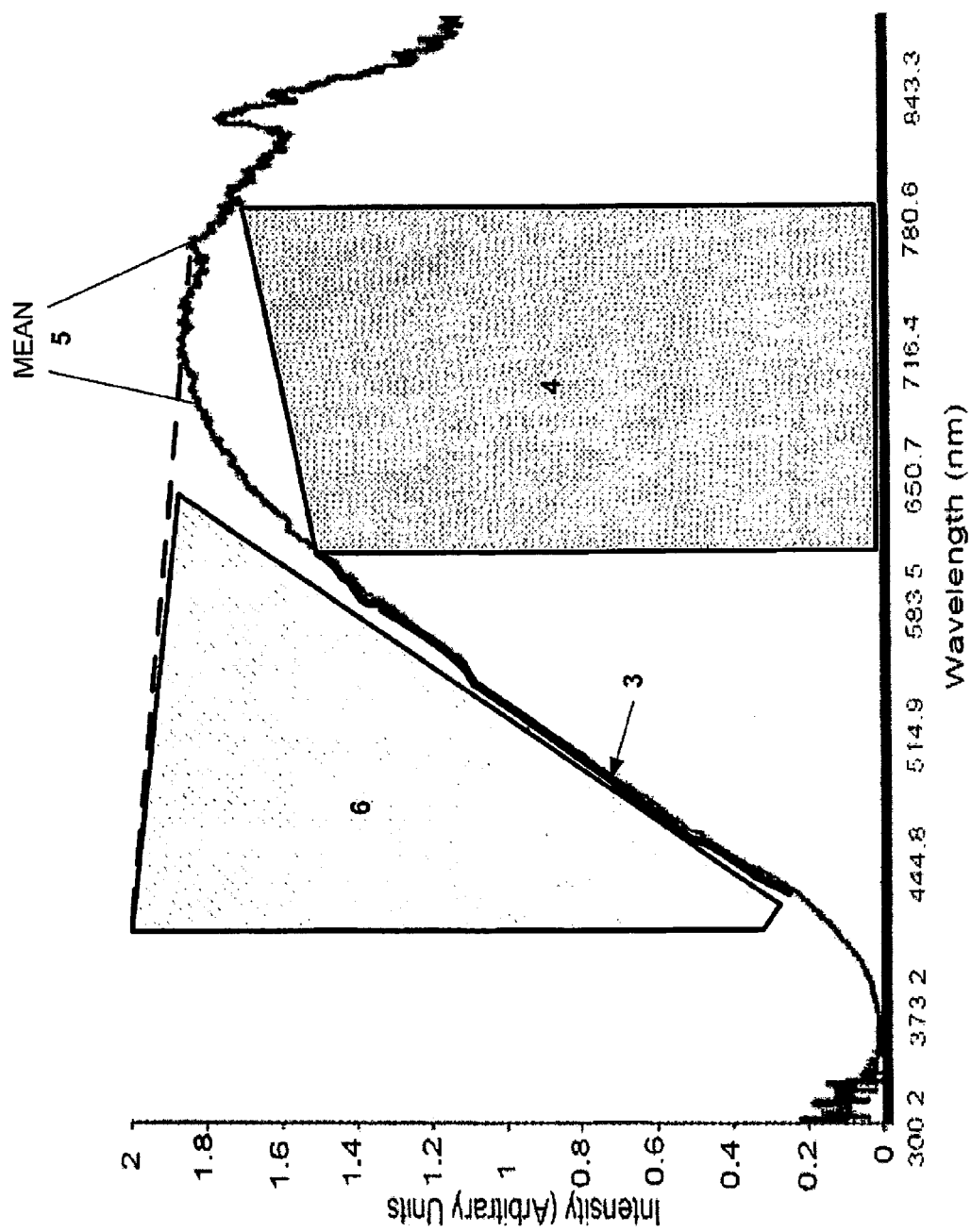
FIG. 2 is a graphical illustration (on an un-normalized lesion spectrum) of the possible modes of scattering spectral analysis using distinctive spectral signatures to determine the presence (or absence) of melanoma according to an embodiment.

FIG. 2 is a graphical illustration (on an un-normalized lesion spectrum) of the possible modes of scattering spectral analysis using distinctive spectral signatures to determine the presence (or absence) of melanoma according to an embodiment. By way of illustration and not by way of limitation, descriminators may be acquired from: the slope of the line 3 joining the intensity a $\lambda=420$ and $\lambda=600$; the area enclosed 4 by the straight line joining the intensity at $\lambda=600$ to the intensity at $\lambda=780$; the mean 5 of the values of intensity between $\lambda=700$ nm and $\lambda=780$ nm; and the area enclosed 6 between $\lambda=420$ nm and $\lambda=780$ nm and the straight line from 420 nm to 780 nm obtained by linearly fitting the intensity in the 700-780 nm range. While the intensity in FIG. 2 is measured over a continuous frequency spectrum, the parameters described above are each prevalent in particular portions of frequency spectrum. Embodiments herein leverage this observation by using discrete sources of illumination for testing suspicious lesions thereby allowing an illumination device to be constructed with a small, pen-like form factor. The selection of light emitters is discussed below. As noted in this embodiment, and without limitation, exemplary illumination and sampling occurs at 420 nm, 600 nm, 700, nm and 780, nm As indicated above, the discriminators may be used in combination to create signatures that are indicative of the presence or the absence of melanoma. By way of illustration, the ratio of the light reflected in the red part of the spectrum (area 4) to the blue portion of the spectrum (area 6) acquired from a suspected lesion may be compared to a range acquired from control samples known to have melanoma. If the measured ratio is within the range established by the control samples, the illumination device 302 may be configured to provide an indication that melanoma has been detected.

In another embodiment, the ratio of equation 1 may be determined in one or more portions of the spectrum. The ratios may be used individually or in combination to create a signature of the presence of melanoma. For example, referring again to FIG. 1, the healthy skin spectrum 2 and the spectrum 1 from the lesion tissue diverge significantly in the blue and red regions of the spectrum. The value of $R_E(\lambda)$ in the blue region of the spectrum will be significantly less than 1 and significantly greater than 1 in the red region of the spectrum. A threshold value may be established for each region based on values obtained from known healthy and unhealthy lesions. In an embodiment, the threshold values are tiered and the measured values compared to the tiered threshold values using alternative boolean expressions. For example, melanoma may be determined when either of the $R_E(\lambda)$ differs from corresponding first tier thresholds or when both differ from second tier thresholds.

Referring again to FIG. 3, the processor 308 executes instructions stored in the memory 310 to initiate a sequence of illuminations. By way of illustration and not by way of limitation, the processor 308 may be responsive to a "start" button (not illustrated) the runs through a pre-selected illuminations using the light emitters from the set of emitters 304. The user may be signaled when the illumination device 302 should be moved. After the device is properly positioned, the user may depress the start button again and the sequence of illuminations repeats. In an embodiment the light 328 is passed through the illumination optical fiber 320 to a termination point that is placed upon the subject lesion 334. The light from the fiber is directed onto lesion 334, where it interacts with the melanin molecules in the lesion 334. A fraction of the scattered light 332 is returned toward the surface of the skin.

The collector optical fiber 322 is positioned next to the source and collects some of the light scattered from the melanin molecules. The collector optical fiber 322 carries the collected light back to a sensor 306, which sensor detects the intensity of the reflected light. By way of illustration and not by way of limitation, the detector may be an avalanche photo diode.

In an embodiment, the processor 308 executes instructions included in memory 310 to determine whether the reflected light is indicative of the presence of melanoma. For example, the processor 308 may output a simple "yes/no" indication to a display device 340 indicating the likely presence or absolute absence of melanoma. This simple indicator will be a clear signal to the user to seek (or not seek) professional diagnosis of the suspect lesion. This simple "yes/no" indication is not meant as a limitation. The yes/no indication may be performed by a light or sound indicator. Alternatively, the processor 308 may provide numeric values to the display device 340 so that the progression of a particular lesion may be assessed by the individual user or the medical professional. The numerical data may be stored in memory 310.

In yet another embodiment, the display device 340 is a computing device, such as, for example, a laptop computer, a desktop computer, and a smartphone. The display device 340 provides additional functionality to the illumination device. For example, the processor 308 may communicate measurement data to the display device 340 which may then communicate the data to a medical professional over a network, such as for example and without limitation the Internet. In an embodiment, a user may send a number of readings over an extended period of time to a medical professional so that a diagnostic can be run each time a value is received. If these values indicate a trend within a particular confidence level, a warning can be sent to the medical professional and to the user of the device that the user or to seek medical attention for the lesion being evaluated.

In an embodiment, the tip of the illumination device is pressure sensitive such that light or sound is emitted when the pen is being pressed too hard (or not firmly enough) onto the skin. This assures that the amount of exsanguinations or blanching (the expulsion of blood from the region to be tested) does not adversely affect the melanoma test. It also assures consistency between multiple readings of the same lesion.

As indicated above, the sensor 306 detects the intensity of light scattered by the lesion under test. In an embodiment, the optical detection is done with a traditional heavily amplified photodiode combined with an analog-to-digital converter (ADC) to allow the analog photodiode to communicate with a digital microcontroller. It is the output signal of the ADC on which the on-board integrated circuits with the programmed analysis algorithms operate. Depending on the activation of the LEDs, the ADC output represents one of the aforementioned spectral analysis categories (individual intensity, slope, or integrated intensity).

Another variation on this embodiment of the present invention is to replace the traditional ADC with an alternative digitizing system. Voltage to Frequency Converters and Current to Frequency Converters (VFC and CFC) has been a mainstay of digital electronics design for many years. By adding a photodiode to the input of a CFC a "digital" photodetector with a large dynamic range is produced. These detectors—capable of monitoring light levels from several thousand LUX (sunny day) to as low as 20 LUX (very dark room)—are fast becoming a mainstay in the medical device community (in pulse oximeters, for example). The digital output is easily interfaced to microcontrollers or signal processors. As the frequency of pulse output is proportional to the incident flux of light data collection is as simple as counting the number of pulses within a fixed time period, or to maintain accuracy the time interval can be dynamic. Pulses are counted until a certain number is reached and the time interval is computed, this allows for a minimum noise threshold to be set but the application must not be time sensitive.

Still another variation on this embodiment disclosed herein is to make the detector a traditional pixelated detector, a CCD. This is used as a direct analog-to-digital converter. All of the light falling on every pixel of the CCD in this variation is summed in CCD control software, and that signal sent to the on-board integrated circuits for analysis with the melanoma detection algorithms.

In an embodiment, the processor 308 consists of one or more memory-integrated circuits (MICs). These circuits are capable of performing the functions of the standard digital integrated circuits, but can also store data and retrieve it, allowing for more complex calculations. This increases the flexibility in implementing the spectral analysis algorithm prescribed to detect the presence of melanoma. Multiple-stage processes involving the use of the output of one circuit as input for another can be realized using MICs as the on-board processors.

In an embodiment, the illumination device 302 is configured as a smart phone add-on detector that connects directly to a smart phone via a USB port or other pin connector. The detector may have its own internal power via a battery that is replaceable or rechargeable. This power source provides power for the light source. Alternatively, the add-on detector may be powered by the internal power source of the smart phone.

The add-on detector comprises fiber-optic probes for delivery of the illumination to the lesion. In an embodiment, the add-on detector is rigidly connected to the smart phone such that the smart phone is brought in intimate contact with the lesion to be analyzed. The sample scattered light can then be collected via the rigidly connected add-on detector. Alternatively, the probe can be flexibly connected to an add-on detector unit such that the probe may be placed appropriately to sample a lesion without the need for maneuvering the entire smart phone device.

The add-on detector interacts with an application on the smart phone that can be downloaded in any fashion known in the art. For example, the melanoma detection application may be downloaded from the Internet and stored on the smart phone. Thereafter, when the application is called, the application may provide instructions to the processor 308 in lieu of, or in addition to, instructions stored in the memory 310.

There are several options for the smart phone application for detection of melanoma. For example, and without limitation, the smart phone application can power the add-on detector for the collection of illumination samples. In this case specific measured amounts of illumination are delivered and the scattered light is detected by the add-on detector. In one embodiment, upon startup of the smart phone application, a communication link is opened to a physician's office computer that prepares to receive the illumination sample from a user. In this case, all of the processing of the illumination sample to determine if melanoma is present is performed at the doctor's office. In this embodiment, the doctor's office controls the determination of whether melanoma is present. The results may be delivered to a doctor for review or, in the alternative, the results may be sent back to the user's cell phone via the open communications channel. Results can be stored at the doctor's office as well as stored on the user's cell phone for viewing.

In an alternate embodiment, all processing can take place on the user's cell phone. In this case, when the application is started, the user places the probe against the lesion to be evaluated, the lesion is irradiated, scattered energy is detected by the fiber-optic probe in the add-on sensor, and calculations associated with the scattered light are made directly on a user's cell phone. In this embodiment, the results may be presented to the user immediately and, optionally, sent over a cell phone communication link to the doctor's office to report results which are indicative of the presence of melanoma.

When a positive sample is determined, that is, the presence of melanoma, that sample may optionally be sent to the doctor's office which can then automatically trigger an appointment being made for the individual to meet with the physician. Scheduling software can then send the appointment information directly back to the user and displayed on the user's cell phone so that the user can be assured that the doctor is informed and that an action plan is underway.

Referring now to FIG. 4 an alternate embodiment is illustrated. In this case a smart phone 904 is connected to a lesion detector unit (LDU) 902. The LDU contains the appropriate illumination sources and probes to illuminate a lesion. A software application is installed on smart phone 904 which actuates the LDU 902 to illuminate a lesion and convey the information to the application for storage on smart phone 904.

The application on smart phone 904 further comprises a communications capability that interacts with the inherent communication capability of smart phone 904 that communicates the results of the spectral detection accomplished by LDU 902 over a normal cellular network via tower 906 over the Internet 908 to a processor 910 that may be located at a doctor's office, a hospital, or other medical care facility.

Processor 910 comprises instructions that cause the processor to analyze the spectral results transmitted from the smart phone 904. The data is processed by the application 912, results are determined by processor 910 and transmitted back to the smart phone 904 to inform the user of the results. Reporting of results can be immediate, or may be stored so that a physician can review the results prior to submitting those results over the network to smart phone 904.

Referring now to FIG. 5, an alternate embodiment is illustrated in this case the lesion detection unit 902 is connected to a laptop computer 914 or other type of mobile device that communicates wirelessly with the Internet with a health care providers processor 910. Analysis and reporting of results to the users laptop 914 is then accomplished in the same manner as referenced in FIG. 9.

Referring now to FIG. 6, an alternate embodiment is illustrated. In this instance the application that can be downloaded to a user's smart phone 904 comprises software instructions that cause the smart phone to manage the operations of the lesion detection unit 902 and to receive spectral results from illumination of a lesion to the processor of the smart phone 904.

In this illustration, the spectral analysis and reporting functionality 912 is part of the application that is stored on smart phone 904. Thus lesion detection unit 902 which can be removably connected to smart phone 904 send results to smart phone 904 which are then analyzed and reported immediately to a user using the display capability of smart phone 904.

In an embodiment, the communication capability of smart phone 904 can be programmed to either automatically report the results over the cellular network 906 to the Internet 908 to a health care providers server 910. When results are reported, the healthcare provider can automatically schedule a follow-up meeting for the user in the event that the spectral analysis and reporting 912 indicates the presence of melanoma.

Referring now to FIG. 7, an alternate embodiment is illustrated. In this embodiment a laptop computer 914 has a spectral analysis and reporting functionality stored in the memory of the laptop computer 914. This functionality comprises instructions that cause the processor of the laptop computer 914 to actuate the lesion detector unit 902 in order to obtain spectral information concerning a lesion of concern. That information is provided to laptop computer 914 which then analyzes the spectral information using the spectral analysis and reporting application 912 stored on the computer 914.

In an embodiment similar to that of FIG. 6, a reporting functionality is implemented that wirelessly transmits the results to an access 916 wherein the results are subsequently provided over the Internet 908 to a health care provider's server. Again based upon the results, appointments can be immediately scheduled for the user.

The microprocessors discussed herein may be any programmable microprocessor, or multiple processor chip or chips that can be configured by software instructions (applications) to perform a variety of functions, including the functions of the various embodiments described above. In the various embodiment illustrated herein, multiple processors may be provided, such as one processor dedicated to wireless communication functions and one processor dedicated to running other applications. Typically, software applications may be stored in the internal memory of the light pen device before they are accessed and loaded into the processor. The processor may include internal memory sufficient to store the application software instructions which would be upgradable so that the latest analysis algorithms could be loaded.

The foregoing method descriptions and the process flow discussions are provided merely as illustrative examples and are not intended to require or imply that the steps of the various embodiments must be performed in the order presented. As will be appreciated by one of skill in the art the steps in the foregoing embodiments may be performed in any order. Words, such as "then," "next," etc., are not intended to limit the order of the steps; these words are simply used to guide the reader through the description of the methods. Although process flow may describe the operations as a sequential process, many of the operations can be performed in parallel or concurrently or in a batch mode as in when multiple collections are made for the same sample of a lesion being illuminated.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

When implemented in software, the functions may be stored as one or more instructions or code on a non-transitory computer-readable or processor-readable storage medium. The steps of a method or algorithm disclosed herein may be embodied in a processor-executable software module which may reside on a computer-readable or processor-readable storage medium. Non-transitory computer-readable or processor-readable media include both computer storage media and tangible storage media that facilitate transfer of a computer program from one place to another. Non-transitory processor-readable storage media may be any available media that may be accessed by a computer. By way of example, and not limitation, such non-transitory processor-readable media may comprise RAM, ROM, EEPROM, or other optical disk storage, magnetic disk storage or other magnetic storage devices, or any other tangible storage medium that may be used to store desired program code in the form of instructions or data structures and that may be accessed by a computer or processor. Additionally, the operations of a method or algorithm may reside as one or any combination or set of codes and/or instructions on a non-transitory processor-readable medium and/or computer-readable medium, which may be incorporated into a computer program product.

Any reference to claim elements in the singular, for example, using the articles "a," "an" or "the," is not to be construed as limiting the element to the singular. The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the invention. Thus, the present invention is not intended to be limited to the embodiments shown herein but is to be accorded the widest scope consistent with the following claims and the principles and novel features disclosed herein.

Figure 8:
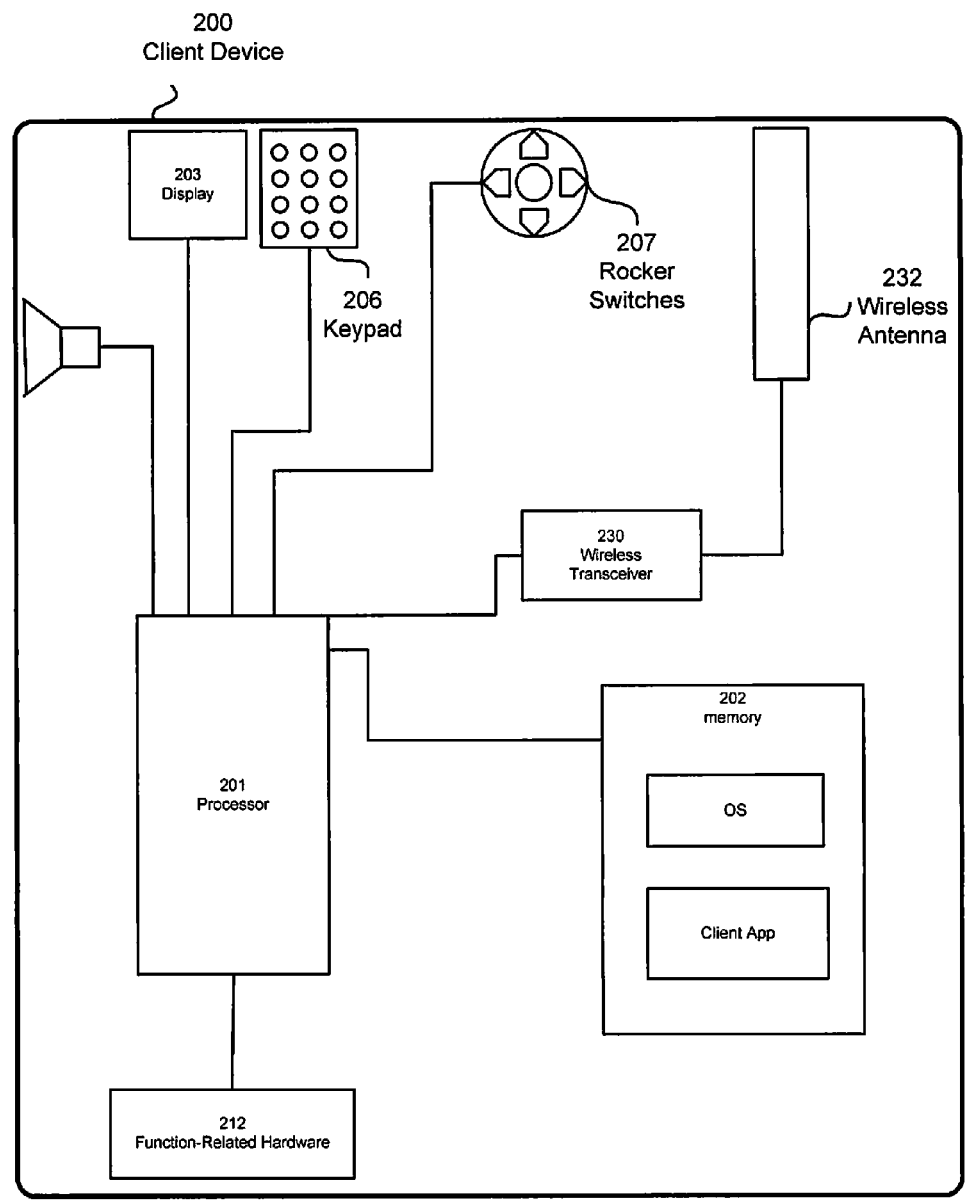
FIG. 8 illustrates an exemplary smart phone of the type useful in the various embodiments.

A typical client device suitable for use with certain embodiments will have in common the components illustrated in FIG. 8. For example, the exemplary client device 200 may include a processor 201 coupled to an internal memory 202 and to a display 203. Client devices typically also include a key pad 206 or miniature keyboard and menu selection buttons or rocker switches 207 for receiving user inputs. A wireless transceiver 230 may be coupled to the processor 201 and an antenna 232 for communicating wirelessly with another device such as a hub. By way of illustration and not by way of limitation, the wireless transceiver may be compliant with Zigbee standards.

Function-related device 212 may also be coupled to the processor 201. For example, if the client device is intended to operate as a printer, the function-related device would be a print engine as known in the art.

The processor 201 may be any programmable microprocessor, microcomputer or multiple processor chip or chips that can be configured by software instructions (applications) to perform a variety of functions, including the functions of the various embodiments described herein. In some client devices, multiple processors 201 may be provided, such as one processor dedicated to wireless communication functions and one processor dedicated to running other applications. Typically, software applications may be stored in the internal memory 202 before they are accessed and loaded into the processor 201. In some client devices, the processor 201 may include internal memory sufficient to store the application software instructions. As part of the processor, such a secure memory may not be replaced or accessed without damaging or replacing the processor. In many client devices, the internal memory 202 may be a volatile or nonvolatile memory, such as flash memory, or a mixture of both. For the purposes of this description, a general reference to memory refers to all memory accessible by the processor 201, including internal memory 202, removable memory plugged into the client device, and memory within the processor 201 itself, including the secure memory.

Figure 9:
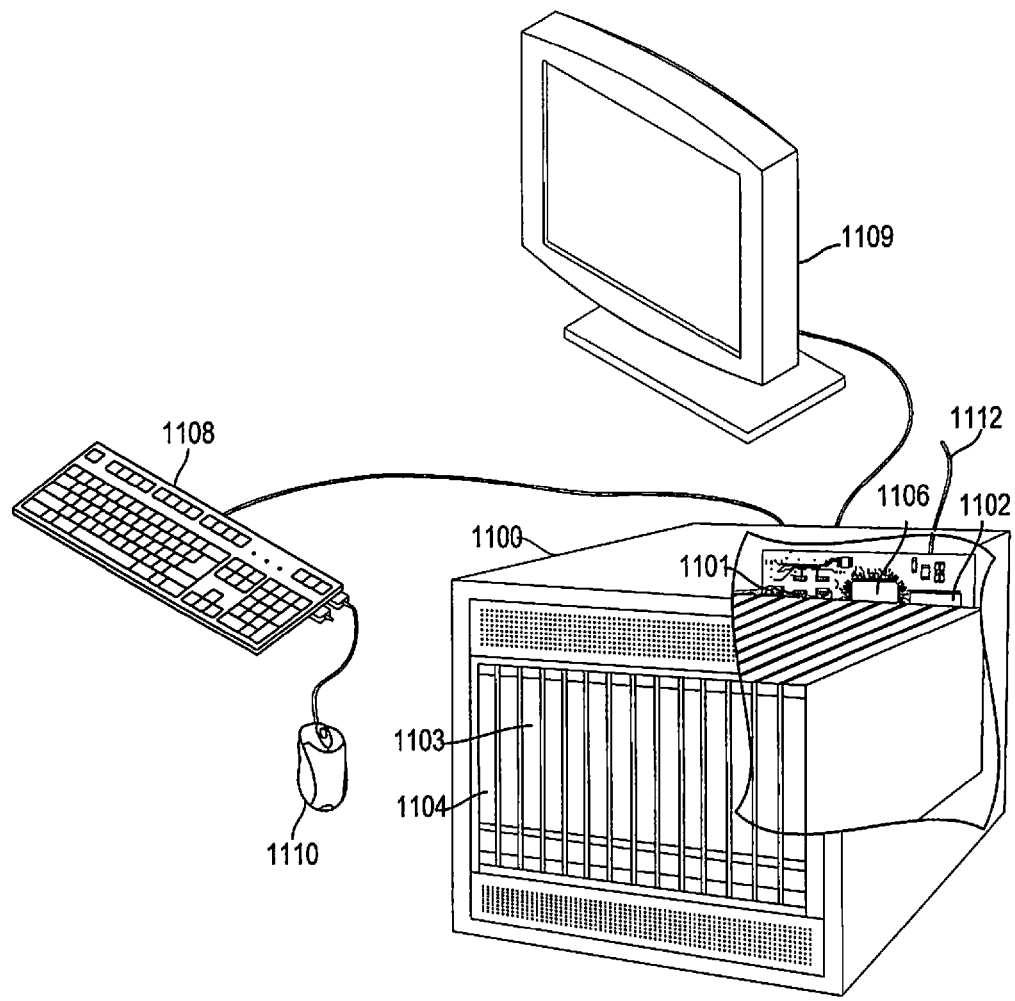
FIG. 9 illustrates a server configuration useful for the various embodiments illustrated.

A number of the embodiments described above may also be implemented on any of a variety of commercially available server devices, such as the server 1100 illustrated in FIG. 9. Such a server 1100 typically includes a processor 1101 coupled to volatile memory 1102 and a large capacity nonvolatile memory, such as a disk drive 1103. The server 1100 may also include a floppy disc drive, compact disc (CD) or DVD disc drive 1104 coupled to the processor 1101. The server 1100 may also include network access ports 1106 coupled to the processor 1101 for establishing data connections with a network 1112, such as the Internet. Server 1100 may also include operator interfaces, such as a keyboard 1108, pointer device (e.g., a computer mouse 1110), and a display 1109.

The processor 1101 may be any programmable microprocessor, microcomputer or multiple processor chip or chips that can be configured by software instructions (applications) to perform a variety of functions, including the functions of the various embodiments described below. Multiple processors may be provided, such as one processor dedicated to wireless communication functions and one processor dedicated to running other applications. Typically, software applications may be stored in the internal memory 1102, 1103 before they are accessed and loaded into the processor 1101. The processor 1101 may include internal memory sufficient to store the application software instructions.

The foregoing method descriptions and the process flow diagrams are provided merely as illustrative examples and are not intended to require or imply that the blocks of the various embodiments must be performed in the order presented. As will be appreciated by one of skill in the art the order of blocks in the foregoing embodiments may be performed in any order. Words such as "thereafter," "then," "next," etc. are not intended to limit the order of the blocks; these words are simply used to guide the reader through the description of the methods. Further, any reference to claim elements in the singular, for example, using the articles "a," "an," or "the," is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of client devices, e.g., a combination of a DSP and a microprocessor, a plurality of microprocessors, one or more microprocessors in conjunction with a DSP core, or any other such configuration. Alternatively, some blocks or methods may be performed by circuitry that is specific to a given function.

In one or more exemplary aspects, the functions described may be implemented in hardware, software, firmware, or any combination thereof. If implemented in software, the functions may be stored on or transmitted over as one or more instructions or code on a computer-readable medium. The blocks of a method or algorithm disclosed herein may be embodied in a processor-executable software module, which may reside on a computer-readable medium. Computer-readable media includes both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a machine readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the invention. Thus, the present invention is not intended to be limited to the embodiments shown herein but is to be accorded the widest scope consistent with the following claims and the principles and novel features disclosed herein.

What is claimed is:

1. A process for optical detection of melanoma lesions comprising:
   illuminating a volume of a segment of skin sequentially with light at a plurality of wavelengths, wherein each of the plurality of wavelengths are within a range of approximately 300 nm and 950 nm;
   receiving an elastic scattering spectrum from the segment of skin at each of the plurality of wavelengths;
   determining a measure of intensity of the received elastic scattering spectrum over the plurality of wavelengths;
   comparing the measure of intensity of the received elastic scattering spectrum over the plurality of wavelengths to a set of spectral signatures indicative of melanoma, wherein at least one of the spectral signatures indicative of melanoma is derived at least in part from:
a ratio of an amount of light scattered by melanoma-containing lesion tissue to an amount of light scattered by healthy skin in each of at least two spectral regions; and
a difference between an average rate of change in the amount of light scattered by the melanoma-containing lesion tissue at a first wavelength and a second wavelength and an average rate of change in the amount of light scattered by the healthy skin at the first wavelength and the second wavelength; and
displaying a message indicative of a presence or absence of melanoma based on the comparing.

2. The process of claim 1, wherein the measure of intensity of the received elastic scattering spectrum comprises a measure of a rate of change of an intensity measure between two of the plurality of wavelengths.

3. The process of claim 1, wherein the measure of intensity of the received elastic scattering spectrum comprises an area determined by two or more of the plurality of wavelengths.

4. The process of claim 1, wherein the plurality of wavelengths are taken from a group consisting of discrete wavelengths in a range of 300-1100 nm at discrete intervals of 1-50 nm.

5. The process of claim 1, wherein illuminating the volume of the segment of skin comprises placing a fiber optic illumination source in contact with the segment of skin and wherein receiving the elastic scattering spectrum from the segment of skin comprises receiving an elastic scattering spectrum from a fiber optic collector.

6. The process of claim 1, wherein displaying the message indicative of the presence or absence of melanoma based on the comparing comprises displaying "yes" to indicate the presence of melanoma and "no" to indicate absence of melanoma.

7. The process of claim 1, wherein displaying the message indicative of the presence or absence of melanoma based on the comparing comprises displaying a numeric value indicating the presence or absence of melanoma.

8. The process of claim 1, further comprising sending result of the comparing to a third-party medical provider.

9. The process of claim 1, wherein the light is generated at the plurality of wavelengths by a discrete narrow-band light source.

10. The process of claim 9, wherein the discrete narrow-band light source is selected from a group consisting of an LED and a laser diode.

11. The process of claim 1, wherein the light is generated at the plurality of wavelengths by filtering a broadband light source.

12. A spectrophotometric apparatus for optical melanoma detection, the apparatus comprising:
two or more light sources;
a display;
a memory having stored thereon a set of spectral signatures that are of melanoma;
a processor configured to perform operations comprising:
receiving a command to scan a segment of skin for the presence of melanoma; and
illuminating the segment of skin sequentially with light at a plurality of wavelengths using the two or more light sources in response to the command, wherein each of the plurality of wavelengths are within a range of approximately 300 nm and 950 nm; and
a detector configured for receiving an elastic scattering spectrum from the segment of skin at each of the plurality of wavelengths,
wherein the processor is further configured to perform operations comprising:
determining a measure of intensity of the received elastic scattering spectrum over the plurality of wavelengths;
comparing the measure of intensity of the received elastic scattering spectrum over the plurality of wavelengths to the set of spectral signatures indicative of melanoma stored in the memory, wherein at least one of the spectral signatures indicative of melanoma is derived at least in part from:
a ratio of an amount of light scattered by melanoma-containing lesion tissue to an amount of light scattered by healthy skin in each of at least two spectral regions; and
a difference between an average rate of change in the amount of light scattered by the melanoma-containing lesion tissue at a first wavelength and a second wavelength and an average rate of change in the amount of light scattered by the healthy skin at the first wavelength and the second wavelength; and
sending a message to the display indicative of a presence or absence of melanoma based on the comparing.

13. The apparatus of claim 12, wherein the plurality of wavelengths are taken from a group consisting of discrete wavelengths in a range of 300-1100 nm at discrete intervals of 1-50 nm.

14. The apparatus of claim 12, wherein the detector is a photodiode coupled to a voltage-to-frequency converter.

15. The apparatus of claim 12, wherein the detector is a photodiode coupled to an analog-to-digital converter.

16. The apparatus of claim 12, wherein the detector is a charged-coupled device.

17. The apparatus of claim 12, wherein the processor is configured such that sending a message to the display indicative of the presence or absence of melanoma based on the comparing comprises sending a message for displaying "yes" to indicate the presence of melanoma and a message for displaying "no" to indicate absence of melanoma.

18. The apparatus of claim 12, wherein the processor is configured such that sending a message to the display indicative of the presence or absence of melanoma based on the comparing comprises sending a message to the display comprising a numeric value indicating the presence or absence of melanoma.

19. The apparatus of claim 12 wherein the processor is further configured to perform operations comprising sending a result of the comparing to a third-party medical provider.

20. The apparatus of claim 12, wherein the two or more light sources are discrete narrow-band light sources.

21. The apparatus of claim 20, wherein the discrete narrow-band light sources are selected from a group consisting of an LED and a laser diode.

22. The apparatus of claim 12, wherein the light is generated at the plurality of wavelengths by filtering a broad-band light source.

23. The apparatus of claim 12, wherein the measure of intensity of the received elastic scattering spectrum comprises a measure of a rate of change of an intensity measure between two of the plurality of wavelengths.

24. The apparatus of claim 12, wherein the measure of intensity of the received elastic scattering spectrum comprises an area determined by two or more of the plurality of wavelengths.

25. The apparatus of claim 12 further comprising a fiber optic transmitter, and wherein the detector comprises a fiber optic collector for elastic scattering spectrum from the segment of skin.

26. The apparatus of claim 12 further comprising an interface to a mobile device.

27. The apparatus of claim 26, wherein the mobile device is taken from a group consisting of a laptop computer, a tablet computer, a smart phone, and a PDA.

28. The apparatus of claim 26, wherein the display comprises a display on the mobile device.

29. The apparatus of claim 26, wherein the processor comprises a processor that is present on the mobile device.

* * * * *